US009526870B2

(12) United States Patent
Simons et al.

(10) Patent No.: US 9,526,870 B2
(45) Date of Patent: Dec. 27, 2016

(54) APPARATUS AND METHOD FOR CONTROLLING VISIBILITY AND ACCESS TO CENTRAL VENOUS ACCESS DEVICES

(71) Applicant: Simons IP, LLC, Carrollton, TX (US)

(72) Inventors: Andrea Simons, Carrollton, TX (US); Brad Simons, Carrollton, TX (US)

(73) Assignee: Simons IP, LLC, Carrollton, TX (US)

( * ) Notice: Subject to any disclaimer, the term of this patent is extended or adjusted under 35 U.S.C. 154(b) by 87 days.

(21) Appl. No.: 14/144,325

(22) Filed: Dec. 30, 2013

(65) Prior Publication Data

US 2014/0188079 A1 Jul. 3, 2014

Related U.S. Application Data

(60) Provisional application No. 61/746,874, filed on Dec. 28, 2012.

(51) Int. Cl.
*A61M 5/32* (2006.01)
*A61M 25/02* (2006.01)

(52) U.S. Cl.
CPC ........ *A61M 25/02* (2013.01); *A61M 2025/026* (2013.01); *A61M 2025/0233* (2013.01)

(58) Field of Classification Search
CPC ............... A61M 2025/0233; A61M 2025/026; A61M 25/02
USPC .................................................. 604/179, 180
See application file for complete search history.

(56) References Cited

U.S. PATENT DOCUMENTS

| 3,160,158 | A |   | 12/1964 | Rayhart |   |
|---|---|---|---|---|---|
| 3,782,378 | A |   | 1/1974 | Page |   |
| 3,827,107 | A |   | 8/1974 | Moore |   |
| 4,470,410 | A |   | 9/1984 | Elliott |   |
| 4,531,942 | A |   | 7/1985 | Turner |   |
| 4,669,458 | A |   | 6/1987 | Abraham et al. |   |
| 4,917,112 | A |   | 4/1990 | Kalt |   |
| 4,966,590 | A | * | 10/1990 | Kalt ...................... | A61M 25/02 128/DIG. 26 |
| 5,380,294 | A |   | 1/1995 | Persson |   |
| 5,605,534 | A |   | 2/1997 | Hutchison |   |
| 5,762,621 | A |   | 6/1998 | Schultz |   |
| 5,817,038 | A |   | 10/1998 | Orange et al. |   |

(Continued)

FOREIGN PATENT DOCUMENTS

WO 2007076069 7/2007

*Primary Examiner* — Kevin C Sirmons
*Assistant Examiner* — Deanna K Hall
(74) *Attorney, Agent, or Firm* — Schultz & Associates, P.C.

(57) ABSTRACT

A device for controlling visibility and access to central venous access devices is comprised of a two-sided body fitted around the torso of a patient. The device has an interior surface and an exterior surface. The interior surface is fitted with a layer of absorbent, wicking material and further includes strips of anti-slip material to fix the device in place. A flexible window is positioned between two lumen retaining flaps and fixed between the interior and exterior surfaces. A pair of indentions is positioned above and below the window. A pair of locking closures is attached to the body over the indentions. The body includes a flexible closure including a resilient gauze section to provide flexibility and size adjustability. The window allows visual access to the intravenous site and prevents patient tampering. The intravenous lines are protected from breakage and tampering by the locking closures, indentions, and lumen retaining flaps.

13 Claims, 4 Drawing Sheets

(56) References Cited

U.S. PATENT DOCUMENTS

| | | | |
|---|---|---|---|
| 5,897,519 A * | 4/1999 | Shesol | A61M 25/02 |
| | | | 602/75 |
| 6,267,115 B1 | 7/2001 | Marshel | |
| D453,831 S | 2/2002 | Inglish | |
| 6,464,669 B2 | 10/2002 | Wilke | |
| 6,645,185 B2 * | 11/2003 | Bird | A61M 25/02 |
| | | | 604/179 |
| 6,832,611 B2 | 12/2004 | Altman | |
| 7,022,111 B2 | 4/2006 | Duplessie et al. | |
| 7,074,982 B2 | 7/2006 | Knutson et al. | |
| 8,123,681 B2 | 2/2012 | Schaeffer | |
| 8,277,419 B1 | 10/2012 | Spitaleri | |
| 2002/0092529 A1 * | 7/2002 | Rozier | A61M 25/02 |
| | | | 128/877 |
| 2005/0020977 A1 | 1/2005 | Eldridge et al. | |
| 2007/0088281 A1 | 4/2007 | Ritchey | |
| 2008/0071224 A1 | 3/2008 | Forsyth | |
| 2009/0054844 A1 | 2/2009 | Alyea et al. | |
| 2011/0288486 A1 | 11/2011 | Rozier et al. | |
| 2012/0046612 A1 | 2/2012 | Scheremet et al. | |
| 2013/0012883 A1 | 1/2013 | Fitzgerald et al. | |
| 2013/0110048 A1 | 5/2013 | Herzog | |

* cited by examiner

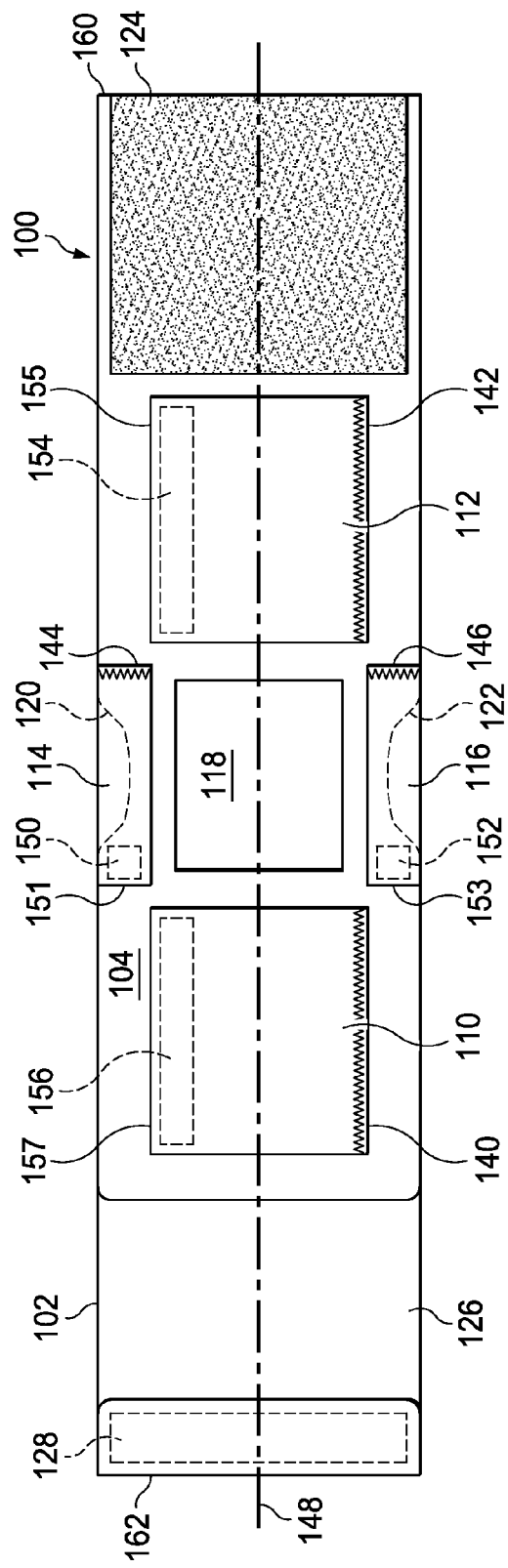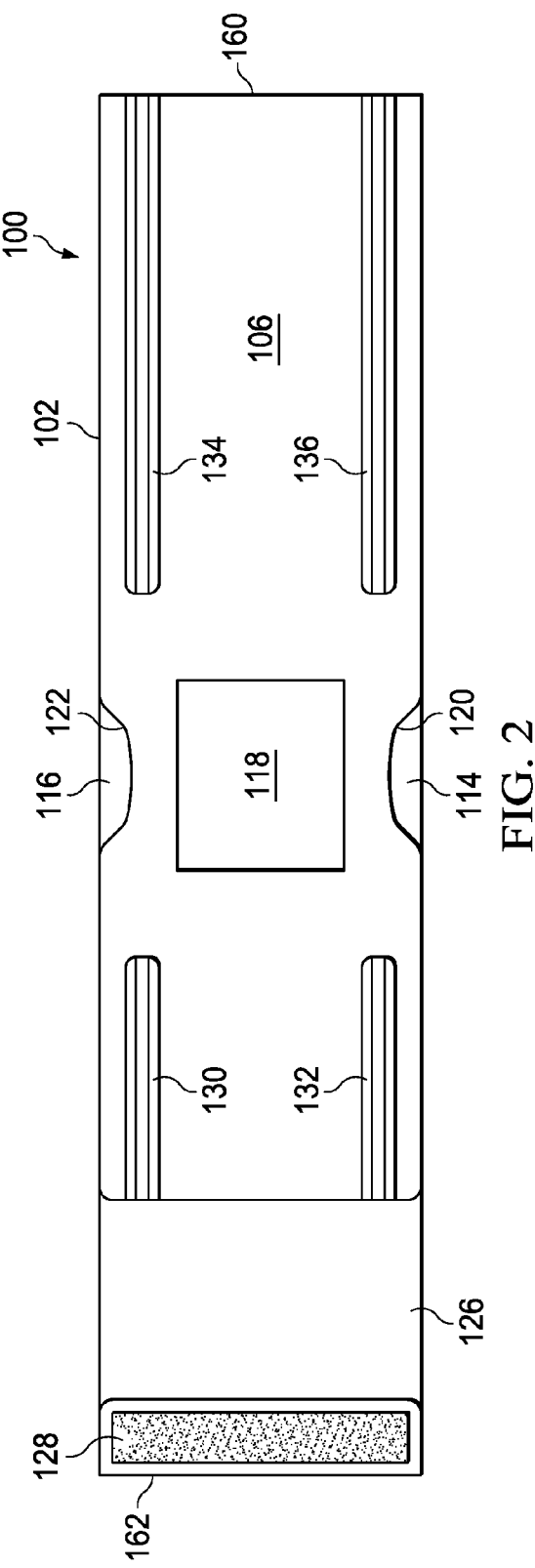

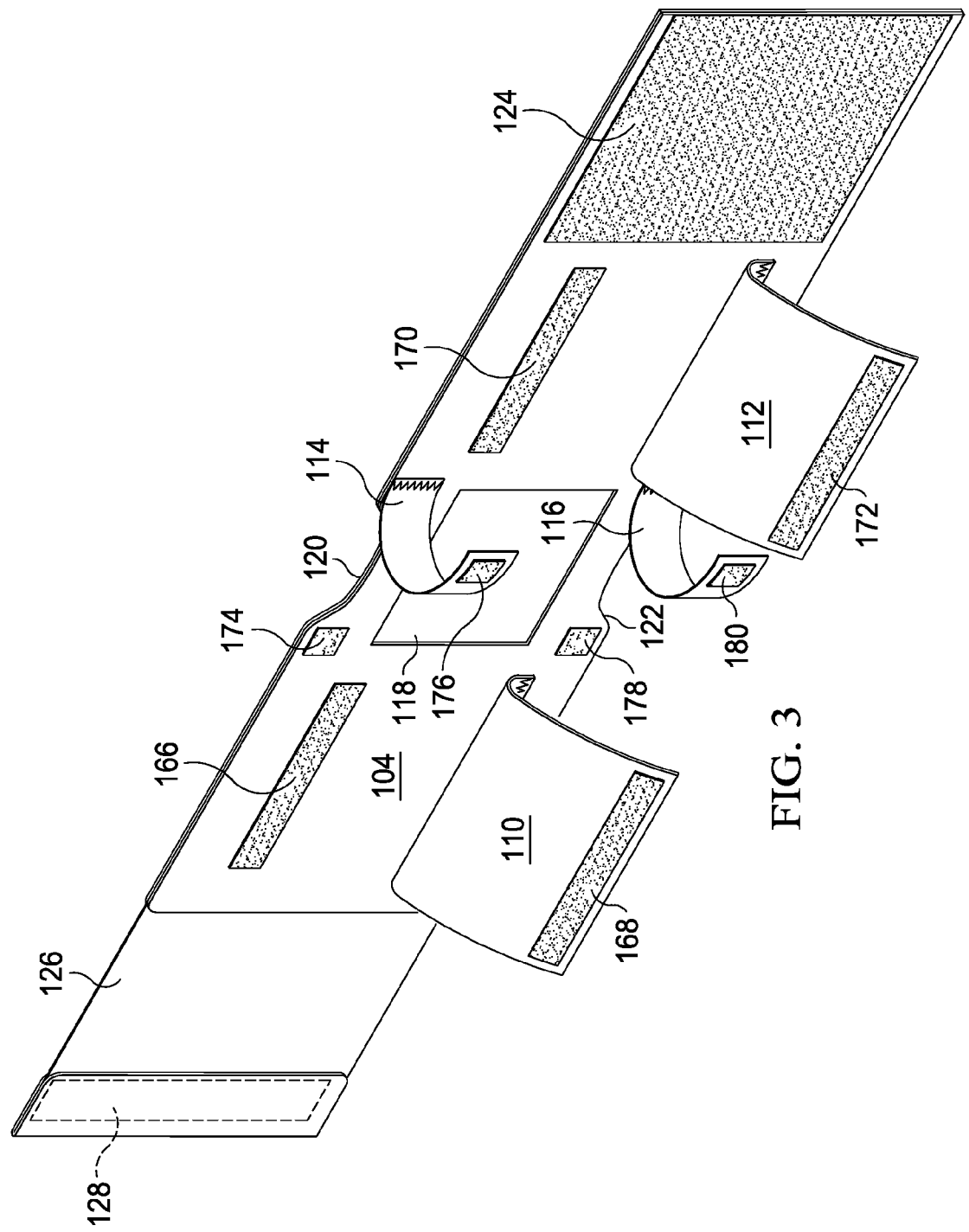

APPARATUS AND METHOD FOR CONTROLLING VISIBILITY AND ACCESS TO CENTRAL VENOUS ACCESS DEVICES

CROSS-REFERENCE TO RELATED APPLICATIONS

This application claims the benefit of U.S. Provisional Patent Application No. 61/746,874 filed on Dec. 28, 2012, the contents of which are incorporated herein by reference.

FIELD OF INVENTION

This disclosure relates to the field of dressing protection for patients fitted with a central venous access device (CVAD). More particularly this disclosure relates to a removable, adjustable, protective device which allows viewing and access to the dressing and shields and compartmentalizes CVAD peripherals without removal from the patient.

BACKGROUND OF THE INVENTION

Disclosed is a device which simultaneously provides the advantages of comfort and flexibility while also providing a highly secure position for tubing and lumens extending from a percutaneous site. In one embodiment, the device is provided for use with patients fitted with central venous access devices (CVAD), gastronomy tubes, or chest tubes. CVADs allow frequent access to the veins without deep needle sticks. Examples of CVADs include central venous catheters (CVC) or central lines, surgically implanted ports, and peripherally inserted central catheters (PICC).

A central venous catheter (CVC) is surgically implanted into a large vein in the neck, chest or groin. A peripherally inserted central catheter (PICC) is inserted into one of the peripheral veins in the upper arm. In addition to the tube inserted into the vein, CVCs and PICCs include lumens. The tube extending from the percutaneous site is often supplied with a central hub or manifold for connection to one or multiple lumens. The lumens, which may or may not be connected to an infusion pump, are used to administer medication or fluids, obtain blood tests, and directly obtain cardiovascular measurements such as the central venous pressure. Venous access devices typically remain in place for extended periods of time. The percutaneous site is dressed and requires routine observation and attention by medical personnel. Typically, while the lumens are not in use they are secured by adhesive tape to the patient to prevent any accidental contact, unwanted movement, and inadvertent removal. The repeated removal of the tape often causes irritation.

When CVADs are used with babies and small children, there is an increased risk that the intravenous tubes and the lumens can be dislodged and contaminated, thus increasing the possibility of bloodstream infections. The disclosed device provides a comfortable fit, is adjustable, allows access to the dressing, redirects and protects the intravenous tubes, and secures the lumens from inadvertent tampering without the use of tape or irritating adhesives.

U.S. Pat. No. 4,470,410 to Elliott discloses a protective retaining device for application to the site of an intravenous or catheter intervention system to protect the site and to retain the tubing in a position proximate the body. The device is comprised of an elongated flexible sleeve. An opening is provided over the intervention site. The sleeve has releasable hook type fasteners, such as Velcro®, and includes a fastenable flap covering the opening. Tubing is secured by the flexible material of the sleeve against the body of the patient.

U.S. Pat. No. 5,897,519 to Shesol, et al. discloses a device for holding tubing in place in a variety of locations. The device comprises a sleeve having a window. The device is fastened by releasable Velcro®. Strips are provided on opposite sides of the window for securing the tubing.

U.S. Pat. No. 6,267,115 to Marshel discloses a flexible sleeve that surrounds an extremity where an intravenous catheter enters a vein. The sleeve is secured with Velcro® and an adhesive layer which adheres to the patient's skin. An opening in the sleeve provides a passage for the tubing. A flexible tab secures the tubing to the sleeve by an adhesive. The device does not include a transparent window.

U.S. Patent Application Publication No. 2005/0020977 to Eldridge, et al. discloses a guard for covering an infusion site while allowing visual inspection. The device is secured with Velcro®. The device provides an opening positioned over the infusion site. A resilient flap having a flexible window is secured to the device over the opening. The flap is also used to secure the tubing. The device does not include a way to redirect tubing or secure lumens.

U.S. Patent Application Publication No. 2013/0012883 to Fitzgerald, et al. discloses a sleeve for protecting and securing catheter dressings and tubes. Velcro® is provided to secure the device to the patient. A slit in the body of the device provides a passage for tubing. A strap secures the tubing against the exterior surface of the device. The device also may include a transparent window positioned over the dressing site.

Therefore, there is a need for a tamper resistant, intravenous protective device that is easily and adjustably secured to a patient. There is also a need for a flexible sleeve which provides comfort to the patient and provides for flexibility to promote physical activity. There is also a need for a device that secures percutaneous tubes and lumens from inadvertent tampering and dislodgment while allowing ease of access for frequent medication.

SUMMARY OF INVENTION

In a preferred embodiment, the device is comprised of a two-sided, flexible body sized to fit around the torso of a patient. The body has an interior surface and an exterior surface. The interior surface is fitted with a layer made of an absorbent, wicking, anti-bacterial material. The interior surface of the body further includes strips of anti-slip material to fix the device in place on the patient. A flexible window is positioned between two lumen retaining flaps. The lumen retaining flaps are permanently attached to the body along one edge. An opposing edge of each lumen retaining flap is adjustably secured to the body via a Velcro® strip. A pair of indentions is positioned above and below the window to allow for nesting of the tubes around the body of the device. A pair of locking closures is attached to the body on the exterior surface directly adjacent the indentions and each can be readily repositioned to completely cover the indentions and any exposed tubing sections. Velcro® is positioned on each end of the body. The Velcro® provides adjustability of the diameter of the device. A resilient gauze section is integrally formed in the body to provide flexibility and encourage air flow.

In use, the device is adjustably fitted to a patient with a percutaneous site from a CVAD, G-tube, or chest tube. The adjustable nature of the device allows for positioning of the window over the site. Because the site is covered by the window, it is kept clean and also prevents patient tampering. Tubes from the percutaneous site are redirected vertically along the medial axis of the patient toward and nested within the indentions. In a preferred embodiment, the tubes are bent around the indentions and releasably secured within them by the locking closures. Velcro® secures the lumen retaining flaps and nucleus hub of the lumens which prevents accidental dislodgment and patient tampering. Each lumen retaining flap, when open, provides access on three sides which allows easy access for an attending caregiver to engage the hub and lumens while the device is in place. The device may be removed from the patient without interfering with the percutaneous site or disconnecting the lumens from the infusion pump.

The device is symmetrical about a longitudinal axis, therefore it is reversible. Reversibility reduces wear and increases the useful life of the device. Further, the flexible nature of the device allows for vigorous patient activity without disturbing the lumens secured under the lumen retaining flaps. The device reduces the use of tape thereby reducing skin irritation and allergic reactions.

A smaller version is provided in an alternate embodiment which is suitable for patients with a surgically implanted PICC line and is envisioned to be fitted around an appendage of the patient.

BRIEF DESCRIPTION OF DRAWINGS

Reference will now be made to the drawings, wherein like parts are designated by like numerals, and wherein:

FIG. 1 is a plan view of the exterior surface of a preferred embodiment.

FIG. 2 is a plan view of the interior surface of a preferred embodiment.

FIG. 3 is an isometric view of a preferred embodiment.

DETAILED DESCRIPTION OF PREFERRED EMBODIMENTS

Figure 4:
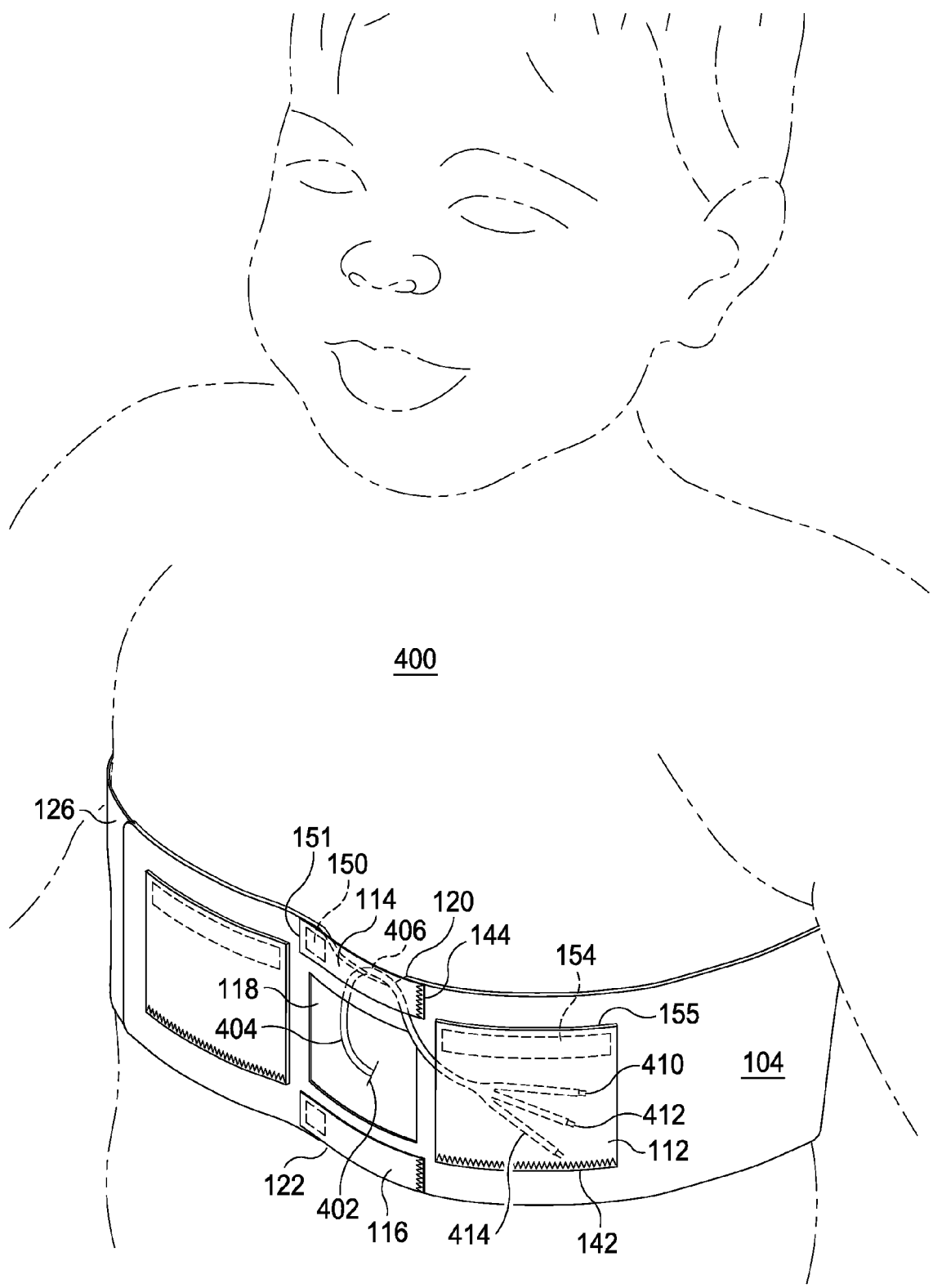
FIG. 4 is an isometric view of a preferred embodiment in place on a patient.

In the descriptions that follow, like parts are marked throughout the specification and drawings with the same numerals, respectively. The drawing figures are not necessarily drawn to scale and certain figures may be shown in exaggerated or generalized form in the interest of clarity and conciseness.

Referring to FIGS. 1 and 2, device 100 is comprised of a two-sided, layered, flexible body 102 having exterior surface 104 and interior surface 106. Body 102 is generally rectangular and symmetrical around longitudinal axis 148. Exterior surface 104 is comprised of primarily durable cotton blend material resistant to abrasion, although cotton and synthetic blends will suffice. Interior surface 106 includes a gusset comprised of a breathable, absorbent material. The interior surface may also comprise an antimicrobial material, agent or surface. In a preferred embodiment, the internal gusset is treated with Silpur Silver Antimicrobial Treatment, available from Thompson Research Associates of Toronto, Ontario, Canada (http://www.ultra-fresh.com/silpure).

Approximately centrally located in body 102 is window 118. In a preferred embodiment, window 118 is a transparent, flexible material such as polyethylene terephthalate (commonly abbreviated PET or PETE). Window 118 is fixed between exterior surface 104 and interior surface 106. The window is fixed in place by sewing. In more rigorous environments, hermetically sealed closures such as adhesive, inductive welding will be used. On exterior surface 104 and adjacent window 118 on two opposing sides of window 118 are lumen retaining flaps 110 and 112. Lumen retaining flap 110 is attached to exterior surface 104 along edge 140. Lumen retaining flap 112 is attached to exterior surface 104 along edge 142. In the preferred embodiment, the lumen retaining flaps are sewn to the body along one edge. However, other methods of attachment such as inductive welding will suffice. End 155 of lumen retaining flap 112 includes fastener 154 to releasably attach end 155 to exterior surface 104. End 157 of lumen retaining flap 110 includes fastener 156 to releasably attach end 157 to exterior surface 104.

Adjacent window 118, on opposing sides, are indentions 120 and 122. In a preferred embodiment, the indentions are also generally rectangular having sides angled at about 45°. The depth of the indentions may be larger or smaller to accommodate different diameters of tubing. The longitudinal axes of the indentions are generally parallel with longitudinal axis 148. Locking closure 114 is attached to exterior surface 104 along edge 144. Locking closure 116 is attached to exterior surface 104 along edge 146. End 151 of locking closure 114 includes fastener 150 to releasably attach end 151 to exterior surface 104. End 153 of locking closure 116 includes fastener 152 to releasably attach end 153 to exterior surface 104. In the preferred embodiment, locking closures 114 and 116 are made of a nylon rope weave for strength and for a low coefficient of friction. Locking closures 114 and 116, when closed, bridge and cover indentions 120 and 122, respectively. The locking closures are positioned to follow the edges of the body and completely cover the indentions.

Body 102 is provided with a flexible closure. The closure allows for adjustment of the circumference of the device to fit different sized patients. At end 160 of body 102 and proximate lumen retaining flap 112 is fastener section 124. Fastener section 124 mates with fastener section 128 on interior surface 106 located at end 162 of body 102. Fastener section 124 is larger than fastener section 128. In the preferred embodiment, fastener sections 124 and 128 and fasteners 150, 152, 154, and 156 are Velcro® type fastening means, but other fasteners such as snaps, buttons, or releasable adhesives will suffice. Adjacent end 162 of body 102 and proximate lumen retaining flap 110 is resilient gauze section 126. Gauze section 126 is comprised of a low-density cotton, spandex weave material which provides ventilation and flexibility to permit patient movement.

Adjacent window 118 are segments of silicon "gripper tape." The gripper tape provides a non-slip surface against the skin of the patient to hold device 100 in place. Segment 130 extends from gauze section 126 towards indention 122 and window 118. Segment 132 extends from gauze section 126 towards indention 120 and window 118. Segment 134 extends from end 160 towards indention 122 and window 118. Segment 136 extends from end 160 towards indention 120 and window 118. Segments 130, 132, 134, and 136 are generally parallel with longitudinal axis 148. Fastener section 128 on end 162 is one half of a typical hook and loop fastener such as Velcro® which mates with fastener section 124 on end 160 from exterior surface 104.

Referring to FIG. 3, lumen retaining flaps 110 and 112 and locking closures 114 and 116 are shown unfastened. Fastener 156 is comprised of fastener section 166 affixed to exterior surface 104 and fastener section 168 affixed to lumen retaining flap 110. Fastener 154 is comprised of fastener section 170 affixed to exterior surface 104 and fastener section 172 affixed to lumen retaining flap 112. Fastener 150 is comprised of fastener section 174 attached to exterior surface 104 and fastener section 176 attached to locking closure 114. Fastener 152 is comprised of fastener section 178 attached to exterior surface 104 and fastener section 180 attached to locking closure 116.

Referring to FIG. 4, device 100 is shown in use. Preferably, device 100 is affixed around the abdomen or chest, in proximity to a percutaneous site the device can be adapted to uses on appendages, the neck, or head.

Device 100 is removably situated so that window 118 is directly above percutaneous site 402. Body 102 is wrapped around patient 400 such that fastener section 128 engages fastener section 124. Fastener section 124 allows for size adjustability of different diameters. The resiliency of gauze section 126 provides additional size adjustability and flexibility.

Segments 130, 132, 134, and 136 are positioned adjacent the skin of the patient and secure the device in position relative to the percutaneous site. Locking closure 114 is detached from exterior surface 104 at end 151. Lumen retaining flap 112 is detached from exterior surface 104 at end 155. Tube 404 extends from percutaneous site 402 adjacent interior surface 106 and is directed in a superior direction generally perpendicular to longitudinal axis 148 towards indention 120. The direction of the tube towards the indention is important. The normal twisting movement of the torso generally causes unwanted damage to the implanted tube if the tube is taped horizontally to the patient. Therefore, directing the tubes to be secured vertically reduces the effect that a twisting movement has on the site. Tube 404 is nested within indention 120 and redirected in an inferior direction towards lumen retaining flap 112. In a preferred embodiment, the tube is positioned centrally within the indention to achieve a maximum of torso rotatability for the patient. End 151 is attached to body 102 via fastener 150. The nylon construction of the locking closure provides low friction for the tube, allowing it limited movement within the confines of the indention and the locking closure, thereby further reducing the deleterious effect of a twisting torso. Tube section 406 redirected around indention 120 is completely covered by locking closure 114, thereby preventing any likelihood of tube section 406 being hooked or grasped. Lumens 410, 412, and 414 attached to the end of tube 404 are placed under lumen retaining flap 112. End 155 of lumen retaining flap 112 is attached to body 102 via fastener 154. Lumens 410, 412, and 414 are stored within and protected by lumen retaining flap 112 to prevent tampering, infection, or dislodgement.

It is understood that any combination of locking closures 114 and 116, indentions 120 and 122, and lumen retaining flaps 110 and 112 could be used alternatively or in conjunction with additional tubes or hubs with equal success. The availability of directly opposing indentions and lumen retaining flaps provides for greater adaptability and ease of use. The open sides of the lumen retaining flaps allow for routing of the tube in the manner most convenient to the caregiver.

Transparent window 118 allows visual inspection of the percutaneous site thereby reducing the need to remove a dressing. Lumens are secured in the lumen retaining flaps on either side of the window to prevent accidental breakage and patient tampering. The lumen retaining flaps allow easy access while the device is place.

The symmetrical construction of the invention allows it to be reversible about an axis generally perpendicular to the longitudinal axis, and the plane of the window, thereby reducing wear and increasing its useful life. The flexibility and "breathability" of the device promotes patient physical activity while keeping the lumens safely retained to prevent infection and dislodgement. Further, securing the lumens reduces skin irritation and potential allergic reactions of the patient. The device may be removed from the patient without disconnecting the lumens from an infusion pump.

Figure 5:
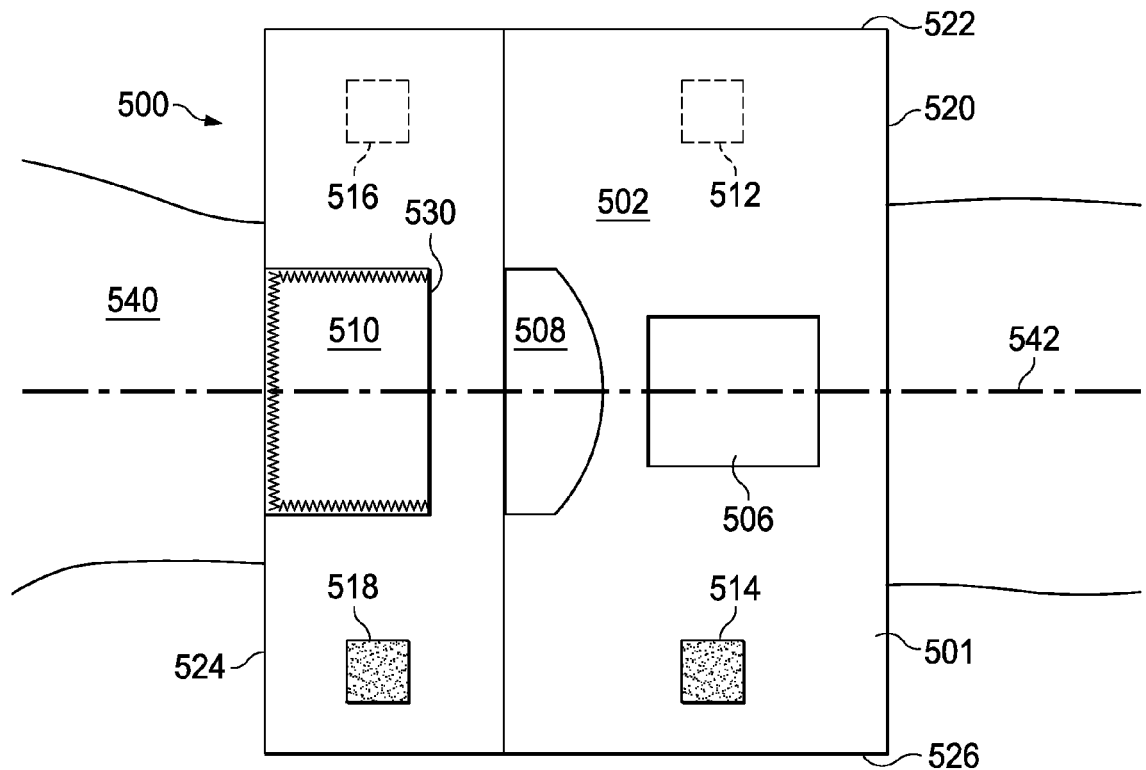
FIG. 5 is a plan view of the exterior surface of an alternate embodiment.
Figure 6:
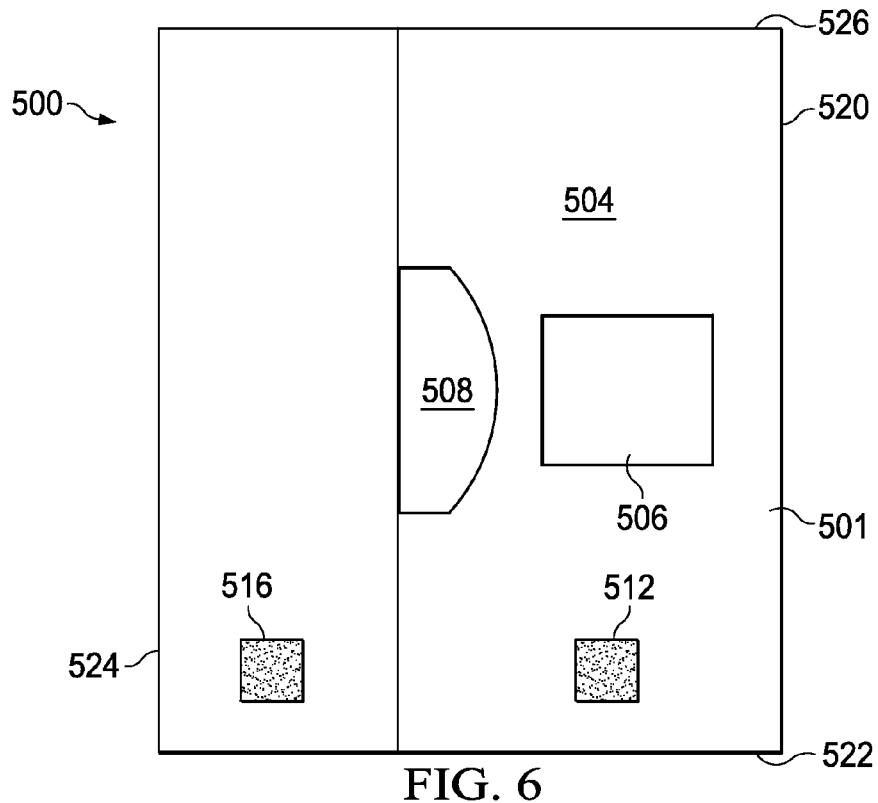
FIG. 6 is a plan view of the interior surface of an alternate embodiment.

Referring to FIGS. 5 and 6, an alternate embodiment, device 500 is shown. Device 500 is primarily manufactured of a cotton material or cotton synthetic blend. Device 500 is comprised of a two layered body 501 having an exterior surface 502 and an interior surface 504. Device 500 is generally applied to smaller, narrower appendages such as arms or legs for use with a PICC line.

Exterior surface 502 includes pocket 510 located proximate end 524 of body 501. Pocket 510 is affixed to exterior surface 502 on three edges. Edge 530 is not affixed to exterior surface 502 and is open. Window 506 is a flexible, transparent layer fixed between exterior surface 502 and interior surface 504. Window 506 is proximate end 520 of body 501. Opening 508 is generally centrally positioned on body 501 adjacent window 506 and pocket 510. Opening 508 passes through body 501 and is visible from both exterior surface 502 and interior surface 504. Proximate end 522 of body 501 and affixed to interior surface 504 are fastener sections 512 and 516. Proximate end 526 of body 501 and affixed to exterior surface 502 are fastener sections 514 and 518. In the preferred alternate embodiment, fastener sections 512, 514, 516, and 518 are hook and loop type fasteners, but alternate fasteners such as snaps, buttons, or adhesive are acceptable.

In use, device 500 is worn on appendage 540 of the patient where ends 522 and 526 are generally parallel with the longitudinal axis 542 of appendage 540. Device 500 is wrapped around appendage 540 such that fastener section 512 engages fastener section 514 and fastener section 516 engages fastener section 518. The intravenous site is covered by window 506 to allow observation of the dressing. A tube exits the intravenous site and passes through opening 508. When lumens attached to the tube are not in use, they are tucked into pocket 510.

It will be appreciated by those skilled in the art that changes could be made to the embodiments described above without departing from the broad inventive concept. It is understood, therefore, that this disclosure is not limited to the particular embodiments herein, but it is intended to cover modifications within the spirit and scope of the present disclosure as defined by the appended claims.

The invention claimed is:

1. An apparatus for securing an intravenous tube and a lumen from an intravenous site comprising:
   a flexible body having a perimeter edge, an interior surface, and an exterior surface;
   a window fixed between the interior surface and the exterior surface;
   a first flap, releasably attached to the exterior surface and adjacent the window;
   a first nesting indention in the perimeter edge;
   a first locking closure, releasably attached to the exterior surface, completely covering the first nesting indention
   a closure attached to the flexible body; and,
   wherein the first nesting indention is configured to redirect the intravenous tube from the interior surface to the exterior surface.

2. The apparatus of claim 1 wherein the intravenous tube is nested in the first nesting indention and is secured by the first locking closure.

3. The apparatus of claim 1 where the interior surface includes an antimicrobial material.

4. The apparatus of claim 1 wherein the flexible body further comprises:
- a second flap, releasably attached to the exterior surface and adjacent the window;
- a second nesting indention in the perimeter edge; and,
- a second locking closure, releasably attached to the exterior surface and adjacent the second nesting indention.

5. The apparatus of claim 1 wherein the first flap further comprises a first flap edge attached to the body and a first opposing flap edge having a first fastener.

6. The apparatus of claim 1 wherein the closure device further comprises:
- a first fastener section affixed to the exterior surface;
- a second fastener section affixed to the interior surface; and,
- a gauze section adjacent the second fastener section.

7. The apparatus of claim 1 wherein the body further comprises an anti-slip section affixed to the interior surface.

8. The apparatus of claim 1 wherein the body is symmetrical along a longitudinal axis.

9. The apparatus of claim 1 wherein the window further comprises a transparent, flexible barrier.

10. An apparatus for securing an intravenous tube and a lumen from an intravenous site comprising:
- a generally rectangular body including a perimeter, an interior surface, an exterior surface, and a longitudinal axis;
- a window fixed between the interior surface and the exterior surface;
- a first indention in the perimeter and a second indention in the perimeter where the first indention and the second indention are adjacent the window;
- a first locking closure having a first locking closure edge, where the first locking closure covers the first indention and the first locking closure edge is attached to the exterior surface;
- a second locking closure having a second locking closure edge, where the second locking closure covers the second indention and the second locking closure edge is attached to the exterior surface;
- a first lumen retaining flap having a first flap edge, where the first flap edge is attached to the exterior surface;
- a second lumen retaining flap having a second flap edge, where the second flap edge is attached to the exterior surface;
- a flexible closure, having a first fastener section affixed to the exterior surface, a second fastener section affixed to the interior surface, and a resilient mesh section adjacent the second fastener section;
- wherein the intravenous tube is positioned in a first direction, where the first direction is generally perpendicular to the longitudinal axis;
- wherein the first locking closure secures the intravenous tube adjacent the first indention; and,
- wherein at least one of the first indention and the second indention is configured to redirect the intravenous tube from the interior surface to the exterior surface.

11. The apparatus of claim 10 where the first and second indentions are generally rectangular and parallel with the longitudinal axis.

12. The apparatus of claim 10 where the first locking closure, the second locking closure, the first lumen retaining flap, and the second lumen retaining flap are releasably connected to the body.

13. The apparatus of claim 10 where the interior surface includes an antimicrobial material.

* * * * *